United States Patent [19]

Riedel et al.

[11] Patent Number: 5,092,323
[45] Date of Patent: Mar. 3, 1992

[54] MOISTURE-ABSORBING, SITE-REVEALING ADHESIVE DRESSING

[75] Inventors: Kenneth E. Riedel, Naperville; Wagdi W. Habib, Barrington; Emil Stempel, Northbrook, all of Ill.

[73] Assignee: Hollister Incorporated, Libertyville, Ill.

[21] Appl. No.: 545,541

[22] Filed: Jun. 29, 1990

[51] Int. Cl.⁵ .................. A61F 13/00; A61F 15/00
[52] U.S. Cl. ..................... 602/54; 128/888; 604/305; 604/307; 602/307
[58] Field of Search .............. 128/155, 887, 888; 604/305, 307

[56] References Cited

U.S. PATENT DOCUMENTS

| | | | |
|---|---|---|---|
| 3,645,835 | 2/1972 | Hodgson | 132/73 |
| 4,399,816 | 8/1983 | Spangler | 128/888 |
| 4,477,325 | 10/1984 | Osborn | 604/336 |
| 4,738,257 | 4/1988 | Meyer et al. | 128/156 |
| 4,793,337 | 12/1988 | Freeman et al. | 128/156 |
| 4,909,243 | 3/1990 | Frank et al. | 128/155 |
| 4,917,112 | 4/1990 | Kalt | 128/155 |
| 4,926,850 | 5/1990 | Lott et al. | 128/155 |

Primary Examiner—Randall L. Green
Assistant Examiner—Paul Prebilic
Attorney, Agent, or Firm—Tilton, Fallon, Lungmus

[57] ABSTRACT

A conformable, gas and vapor permeable, moisture-absorbing adhesive dressing particularly suitable for use as a skin-protecting covering over and about an intravenous injection site. The dressing includes a thin, stretchable, and conformable base layer of moisture-absorbing skin barrier material having both dry and wet tack and having a generally central site-inspection opening therethrough, and a thin, transparent, and conformable cover layer formed of a gas and vapor permeable polymeric film having an underside coated with a gas and vapor permeable layer of pressure-sensitive adhesive that secures the film to the upper surface of the base layer and to a patient's skin in the area defined by the opening in the base layer. An arrangement of release sheets covers the underside of the dressing, such sheets being formed and folded to facilitate application of the dressing to a wearer.

15 Claims, 1 Drawing Sheet

MOISTURE-ABSORBING, SITE-REVEALING ADHESIVE DRESSING

BACKGROUND AND SUMMARY

Co-owned U.S. Pat. Nos. 4,477,325 and 4,738,257 disclose soft, conformable, cross-linked skin barrier compositions, and occlusive dressings utilizing such compositions, having both wet and dry tack and having a moisture-absorbing hydrocolloid phase dispersed therein. A variety of other conformable, moisture-absorbing skin barrier materials similarly capable of adhering to the skin even in the presence of moisture have been disclosed in the prior art and are well known in the medical field.

Transparent, stretchable, vapor-permeable, adhesive-coated films are also known in the medical field as disclosed, for example, in U.S. Pat. No. 3,645,835. Such adhesive films have been widely employed in the construction of incise drapes, transparent dressings, burn and wound covers, and the like.

It is a common practice to utilize conventional medical-grade adhesive tape to secure intravenous (IV) tubulature in place at injection sites. Strips of tape are customarily placed over the tubing at the site to hold it against the skin and prevent unintended extraction should pulling forces be applied to such tubing. It has also been known to utilize stretchable, vapor-permeable, adhesive-coated films as protective covers at such injection sites to help retain the IV tubes or catheters in place and, in particular, to protect the sites against contamination and infection.

While such films often provide the desired protective function, the presence of moisture, particularly for a patient experiencing diaphoresis, may weaken the adhesive seals or prevent such seals from occurring in the first instance. Such a problem also frequently occurs in the attachment and/or retention of conventional adhesive tapes, with the result that films or tapes applied to help hold an IV tube or catheter in place may fail to perform the intended immobilization functions and, at least in some cases, place patients at risk.

We have made attempts to utilize skin-barrier pads as the means for holding IV tubes in place. While such pads may be superior to adhesive tapes and films because of their wet tack and moisture-absorbing capabilities, they are generally opaque or non-transparent, making inspection of the injection sites to ascertain bleeding, phlebitis, or other complications difficult or impossible without pad removal. Such pad removal and replacement is time-consuming, expensive, and increases the risks of site contamination.

Therefore, an important aspect of this invention lies in providing a site-revealing, moisture-absorbing, adhesive dressing that is particularly suitable as a protective cover for IV injection sites and overcomes the aforementioned shortcomings and disadvantages of prior products and procedures. Specifically, a main aspect of this invention lies in providing a dressing that is stretchable and may therefore be placed over an injection site to conform well with the contour of an IV tube or catheter and surrounding areas of skin, that adheres well to the skin and to the IV tube or catheter, that absorbs moisture from the skin about the injection site, that releases such moisture to atmosphere at controlled rates and that is also permeable to oxygen and carbon dioxide, and that permits visual inspection of the injection site while the dressing is in place.

Briefly, the adhesive dressing of this invention takes the form of a conformable pad having a thin base layer of stretchable, moisture-absorbing skin barrier material having both wet and dry tack and having a site-inspection opening extending therethrough, a transparent cover layer composed of a thin, stretchable polymeric film that is non-permeable to liquid water but that has both gas and moisture vapor permeability, such cover layer extending over the base layer and its opening and having its underside coated with a clear layer of gas and vapor permeable pressure-sensitive adhesive. Since both the cover layer and its adhesive coating are transparent, the dressing may be readily oriented and applied so that an injection site is visible through the opening in the relatively opaque base layer and, because of its stretchability, the portion of the cover layer spanning that opening will readily conform and adhere to the tubulature in the area of the injection site. Since the cover layer is imperforate and serves as a bacterial barrier, it effectively protects the injection site and the area of skin covered by the dressing from contamination. At the same time, the gas and vapor permeable cover layer is "breathable" and therefore permits respiration through the dressing. Adherence of the dressing is assured because of the wet tack capabilities of the base layer and because the skin barrier material from which the base layer is formed is capable of absorbing moisture. Thus, the base layer absorbs moisture in liquid form (i.e., perspiration) and the cover layer then relieves the base layer of its moisture content by transmitting such moisture in vapor form to atmosphere.

To serve effectively as a vapor-transmitting dressing, the cover layer and its adhesive layer should have water vapor transmission characteristics of at least 300 grams per square meter over 24 hours at 40° C. and at 80% relative humidity. The thickness of the base layer should fall within the general range of about 0.25 to 0.50 millimeters (10 to 20 mils) and the thin, stretchable cover layer should have a thickness within the range of about 0.025 to 0.050 millimeters (1 to 2 mils). The size of the dressing may vary according to needs but, where used as an IV dressing, the planar measurement in any given direction should fall within the range of about 5 to 10 centimeters (2 to 4 inches).

The underside of the dressing is backed by removable backing means in the form of a pair of release sheets, each sheet being folded along a transverse fold line with the fold lines of the two sheets extending alongside each other across the opening in the base layer. The fold lines provide each release sheet with a tab portion that may be gripped by a user to peel the release sheets away from the dressing and thereby facilitate application of the dressing over and about an injection site.

DRAWINGS

DETAILED DESCRIPTION OF PREFERRED EMBODIMENT

Figure 1:
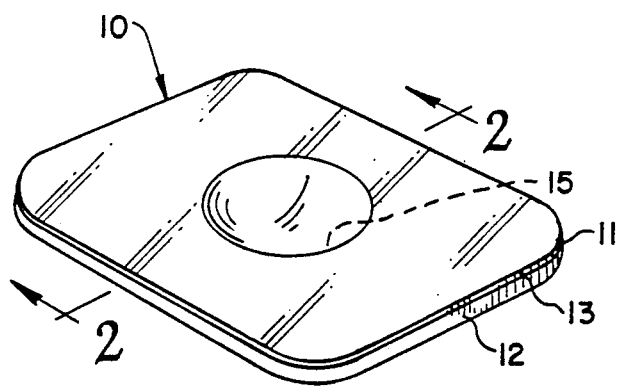
FIG. 1 is a perspective view of an occlusive dressing embodying the present invention.

Referring to the drawings, the numeral 10 designates an occlusive dressing in the form of a pad or patch 11 having three layers: a base layer 12, a thin cover layer 13, and an adhesive layer 14. Because of the thinness of the layers and the materials from which they are formed, the dressing is compliant and conforms readily to the contours of the body and tubulature at an IV injection site.

Base layer 12 is formed from a soft, comformable, water-absorbing skin barrier material having both wet and dry tack. While various materials, all commonly known as "skin barrier" materials, may be used, particularly effective results have been obtained utilizing a skin barrier material formulated from a mixture of elastomers and hydrocolloids as described in co-owned U.S. Pat. Nos. 4,738,257 and 4,477,325. There, polyisobutylene is employed as one elastomeric ingredient blended with a cross-linking elastomeric resin. Cross-linkable resins which blend with polyisobutylene to form a continuous elastomeric phase include the copolymer resins formed from ethylene and vinyl acetate (EVA resins). The proportions of ethylene to vinyl acetate may be varied, although effective results may be achieved if from 40 to 60 parts of vinyl acetate are copolymerized with 60 to 40 parts by weight of ethylene.

The EVA copolymers may be cross-linked by gamma irradiation. For example, a Cobalt-60 radiation source may be used to apply from 1.0 to 8.0 megarads. A desirable degree of cross-linking is obtainable with applied gamma irradiation of 2 to 4 megarads. Optionally, a minor amount of an additional cross-linking resin may be included, such as an acrylamide polymer which reacts with EVA to form cross links. In the preferred formulations, the cross-linked network is formed essentially from the EVA polymer by irradiation of an EVA-containing elastomeric phase.

To provide for fluid absorption, the barrier material may contain a relatively high proportion of hydrocolloid and also a super-absorbent type hydrocolloid. Super-absorbents can be formed from starch and acrylonitrile, the starch, either gelatinized or in grannular form, being reacted with the acrylonitrile under alkaline conditions. For example, the resulting products may comprise a starch-polyacrylonitrile graft polymer, as described in U.S. Pat. Nos. 3,997,484 and 3,661,815. Synthetic super-absorbents may also be utilized, such as sodium polyacrylates.

The hydrocolloids which may be employed alone or in combination with a super-absorbent include pectin, carboxymethylcellulose, such as sodium CMC, karaya, gelatin, guar, etc. The hydrocolloid mixture may include both natural vegetable hydrocolloid gums and synthetic hydrocolloids; for example, a mixture of pectin and sodium CMC has been found to be particularly suitable, especially when used in admixture with a super-absorbent such as sodium polyacrylate.

While U.S. Pat. Nos. 4,447,325 and 4,738,257 (the disclosures of which are incorporated by reference herein) are believed to disclose preferred compositions for forming the base layer 12 of dressing 10, it is to be understood that other skin barrier materials having somewhat similar properties are known and may be used. For proper conformability the planar barrier layer should be relatively thin, having a thickness falling generally within the range of about 0.25 to 0.50 millimeters (0.010 to 0.020 inches, or 10 to 20 mils). A thickness of approximately 0.375 millimeters (0.015 inches, or 15 mils) is believed preferable.

The base layer 12 has a generally centrally located site-inspection opening 15. The opening has smoothly curved arcuate edges and is preferably circular in shape. Where the dressing is to be used for injection sites, the opening should have a diameter within the general range of 2.5 to 5.0 centimeters (1 to 2 inches), and the dressing itself should have a maximum width or outside dimension measured in any direction along the plane of the dressing of approximately 5 to 10 centimeters (2 to 4 inches).

The cover layer 13 comprises a thin, compliant film formed of any of a number of gas and vapor permeable polymeric materials. The film is occlusive with respect to particulates and bacteria; however, it should be capable of transmitting both water vapor and gases such as oxygen and carbon dioxide. The film of the cover layer should also be stretchable, preferably having a degree of elongation of at least 130%.

Thermoplastic films having such characteristics are known in the medical field. Reference may be had to U.S. Pat. No. 3,645,835 for the description of a polyurethane film having such properties. Other films having similar properties may be extruded from a class of elastomeric resins that are polyether block amides such as those marketed by Bertek, Inc. under the designation "Medifilm 810." The cover film may alternatively be formed of any of various polyesters such as the copolymers of various cyclic polyesters including duPont's "Hytrel" and General Electric's "Lomod," both of which are copolymers of polyether prepolymers, polybutylene terephthalate and polyisobutyl terephthalate, respectively.

Figure 2:
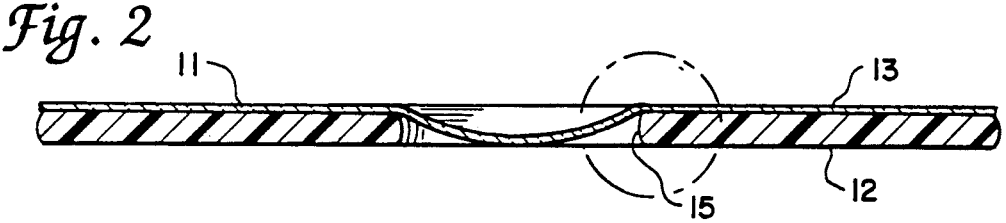
FIG. 2 is an enlarged cross sectional view taken along line 2—2 of FIG. 1.
Figure 3:
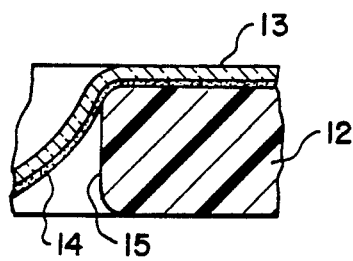
FIG. 3 is a further enlarged fragmentary sectional view of a portion of the dressing indicated in FIG. 2.

The imperforate cover layer 13 should be relatively thin, generally having a thickness within the range of 0.025 to 0.050 millimeters (0.001 to 0.002 inches, or 1 to 2 mils). Because of its thinness and stretchability, the film cannot bridge the opening 15 in the base layer 12 without sagging when the dressing is oriented as shown in FIGS. 1-3. Such conformability means that that portion of the cover layer traversing opening 15 will readily extend into contact with the skin surface and other surfaces visible through opening 15.

Adhesive layer 14 coats the underside of cover layer 13. Any relatively clear hypoallergenic medical-grade pressure-sensitive adhesive having the necessary gas and vapor transmission characteristics may be used. Medical-grade acrylic copolymer adhesives are well known and are believed particularly effective for this purpose. The adhesive layer, combined with cover layer 13, should provide sufficient transparency so that an injection site may be clearly viewed through layers 13 and 14 extending across opening 15. In addition, the combined layers 13 and 14 should have water vapor transmission characteristics of at least 300 grams per square meter over 24 hours at 40° C. and at 80% relative humidity. Preferably such WVTR values be within the range of 350 to 375 grams per square meter so as to exceed the transmission characteristics of healthy skin without at the same time causing excessive drying at the injection site.

Figure 4:
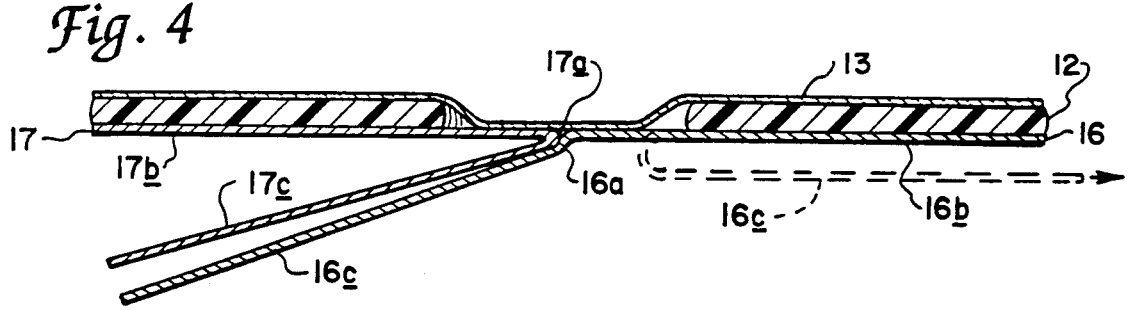
FIG. 4 is a sectional view similar to FIG. 2 but depicting the dressing with its backing means intact but with an initial removal step being depicted in broken lines.

Dressing 10 requires suitable backing means to protect the tacky undersides of base layer 12, and the adhesive coating 14 of cover layer 13 within opening 15, until application of the dressing to a patient. In the preferred embodiment shown, such backing means takes the form of a pair of release sheets 16 and 17 (FIG. 4). Each sheet has a transverse fold line 16a, 17a, the two fold lines being disposed immediately adjacent each other and extending in parallel across the underside of the dressing beneath opening 15. The fold line of each sheet constitutes the demarcation between the dressing-contacting section 16b, 17b and the tab portion 16c, 17c of that sheet. As shown in FIG. 4, the tab portions of the two release sheets may extend in side-by-side relation and may angle downwardly away from the dressing at any of a variety of angles; however, when the dressing is in packaged condition, it will be understood that the two tab portions together lie folded beneath one or the other of the dressing-contacting portions 16b or 17b.

Figure 5:
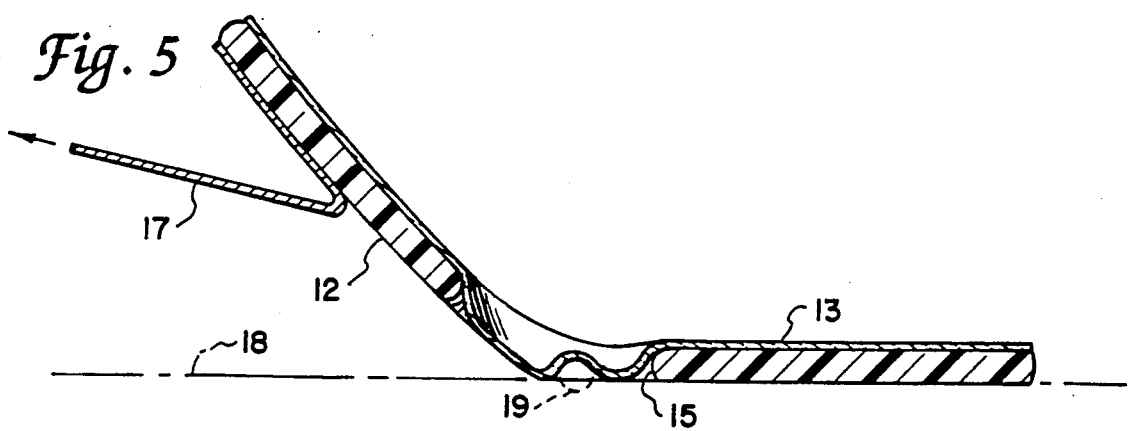
FIG. 5 shows the dressing after initial attachment of the dressing to an injection site and during the final step of removing the second release sheet.

The release sheets, which may be formed of paper, plastic film, or any other suitable material, have their upper surfaces coated with a release agent such as silicone. Therefore, at the time of use, such sheets may be readily peeled away from the underside of the dressing (including the adhesive-coated underside of the transparent cover layer 13 extending over opening 15) to permit adhesive application of the dressing to the patient. While application techniques may vary, it is generally preferred to commence peeling back one of the release sheets, such as sheet 16 depicted in broken lines in FIG. 4, to expose the injection site through the adhesive-coated transparent cover film 13 extending over opening 15. The dressing is then lowered into contact with the patient's skin, designated by numeral 18 in FIG. 5, the other release sheet 17 is peeled away, and the remainder of the dressing is brought into contact with the patient's skin. The highly compliant cover film, and the adhesive coating along its underside, contact the patient's skin that remains visible through opening 15 and, as indicated in FIG. 5, such film readily follows the contour of an intravenous catheter 19 at the injection site.

It is to be noted that although film 13 is highly compliant, base layer 12 supplies enough structural stability to the film, upon removal of release sheets 16 and 17, to prevent adjacent portions of the film's adhesive undersurface from contacting each other and forming wrinkles during application of the dressing. The portion of the film 13 bridging opening 15 may therefore be laid smoothly over the injection site without wrinkles or creases that might obscure inspection of the site through transparent film.

The result is a dressing which effectively holds the catheter in position while at the same time allowing visual inspection of the injection site. The site remains covered and protected against contamination while still permitting transmission of water vapor and gases. Perspiration from the skin is absorbed by base layer 12 and converts to vapor form along the edges (including the edges of opening 15) and upper surface of the base layer where it is then free to diffuse through adhesive layer 14 and cover layer 13.

While in the foregoing we have disclosed an embodiment of the invention in considerable detail for purposes of illustration, it will be understood by those skilled in the art that many of these details may be varied without departing from the spirit and scope of the invention.

We claim:

1. An adhesive dressing comprising a thin base layer of stretchable and conformable moisture-absorbing skin barrier material having both wet and dry tack; said base layer having a site-inspection opening extending therethrough; a cover layer composed of a thin, stretchable, and transparent polymeric film, non-permeable to liquid water but having both gas and moisture vapor permeability, covering said base layer and said opening; said cover layer having an underside coated with a layer of gas and vapor permeable pressure-sensitive adhesive; said adhesive layer extending across said opening and being in direct contact with a patient's skin through said opening when said dressing is in use.

2. The dressing of claim 1 in which said cover layer and said adhesive layer together have water vapor transmission characteristics of at least 300 grams per square meter over 24 hours at 40° C. at 80% relative humidity.

3. The dressing of claim 2 in which said water vapor transmission characteristics fall within the range of 350 to 375 grams per square meter over 24 hours at 40° C. at 80% relative humidity.

4. The dressing of claims 1 or 2 in which said base layer has a thickness within the range of about 0.25 to 0.50 millimeters.

5. The dressing of claim 4 in which said thickness of said base layer is about 0.375 millimeters.

6. The dressing of claims 1 or 2 in which said cover layer has a thickness within the range of about 0.025 to 0.050 millimeters.

7. The dressing of claims 1 or 2 in which said base layer has a composition consisting essentially of an elastomeric phase integrated by a cross-linked polymer network and a particulate water-absorbing hydrocolloid phase dispersed in said cross-linked elastomer phase.

8. The dressing of claims 1 or 2 in which said cover layer comprises a film of polyurethane.

9. The dressing of claims 1 or 2 in which said dressing comprises an IV dressing having a maximum dimension in outline within the range of 5 to 10 centimeters.

10. The dressing of claim 9 in which said site-inspection opening has an arcuate border.

11. The dressing of claim 10 in which said opening is generally circular.

12. The dressing of claim 1 in which said base layer has an underside; said undersides of said base layer and said cover layer within said opening being backed by removable backing means capable of being peeled from said undersides for attachment of said dressing to a patient.

13. The dressing of claim 12 in which said backing means comprises a pair of release sheets each folded along a transverse fold line to provide a dressing-contacting section and a tab section; said dressing-contacting section of each release sheet contacting said undersides of said base layer and said cover layer within said opening.

14. The dressing of claim 13 in which said fold lines are parallel and disposed immediately adjacent to each other, and extend beneath said dressing across said opening.

15. The dressing of claim 14 in which said tab portions extend alongside each other in parallel planes.

* * * * *